United States Patent
Li et al.

(10) Patent No.: US 8,501,457 B2
(45) Date of Patent: *Aug. 6, 2013

(54) **ENRICHMENT OF *LISTERIA* SPP**

(75) Inventors: Jun Li, Baltimore, MD (US); Win Den Cheung, Olney, MD (US)

(73) Assignee: Samsung Techwin Co., Ltd., Changwon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,469

(22) Filed: Jun. 8, 2011

(65) Prior Publication Data

US 2012/0052555 A1    Mar. 1, 2012

Related U.S. Application Data (60) Provisional application No. 61/378,099, filed on Aug. 30, 2010.

(51) Int. Cl.
*C12N 1/20*    (2006.01)

(52) U.S. Cl.
USPC ....................................... 435/253.6

(58) Field of Classification Search
None
See application file for complete search history.

(56) References Cited

U.S. PATENT DOCUMENTS 6,228,606 B1 * 5/2001 Facon et al. ............... 435/34
2011/0159515 A1 * 6/2011 Stimson ................... 435/7.1

FOREIGN PATENT DOCUMENTS

EP    0949266 A1 * 10/1999

OTHER PUBLICATIONS

AOAC Official Method for the detection of *L. monocytogenes* in foods, 2006, http://www.aoac.org/omarev1/2003_12.pdf.*
Tsai and Hodgson, Development of a synthetic minimal medium for *Listeria monocytogenes*, Appl. Environ. Microbiol. 2003, 69 (11): 6943.*
Busch and Donnelly, Development of a repair-enrichment broth for resuscitation of heat-injured *Listeria monocytogenes* and *Listeria innocua*, Appl. Environ. Microbiol. 1992, 58(1): 14.*
Cox et al., Food Microbiol. 7: 311-325 (1990).*
Dykes et al., Lett. Appl. Microbiol. 35: 538-542 (2002).*

* cited by examiner

*Primary Examiner* — Patricia A Leith
*Assistant Examiner* — Erin M Bowers
(74) *Attorney, Agent, or Firm* — Sughrue Mion, PLLC (57) ABSTRACT

A medium for enriching *Listeria* spp. without polymerase chain reaction (PCR) inhibition and a method of using the medium.

8 Claims, 8 Drawing Sheets

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
tccaagcagt gagtgtgaga a                                                21

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2
tgacagcgtg aaatcagga                                                   19

<210> SEQ ID NO 3
<211> LENGTH: 21
<212> TYPE: DNA
<213> ORGANISM: Artificial Sequence
<220> FEATURE:
<221> NAME/KEY: misc_feature
<222> LOCATION: (14)..(14)
<223> OTHER INFORMATION: ribonucleotide
<220> FEATURE:
<223> OTHER INFORMATION: Synthetic construct

<400> SEQUENCE: 3
ccatcacagc tcaugcttcg c                                                21

<210> SEQ ID NO 4
<211> LENGTH: 224
<212> TYPE: PRT
<213> ORGANISM: Pyrococcus furiosus

<400> SEQUENCE: 4

Met Lys Ile Gly Gly Ile Asp Glu Ala Gly Arg Gly Pro Ala Ile Gly
 1               5                  10                  15

Pro Leu Val Val Ala Thr Val Val Asp Glu Lys Asn Ile Glu Lys
                20                  25                  30

Leu Arg Asn Ile Gly Val Lys Asp Ser Lys Gln Leu Thr Pro His Glu
            35                  40                  45

Arg Lys Asn Leu Phe Ser Gln Ile Thr Ser Ile Ala Asp Asp Tyr Lys
        50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala

```
                130                 135                 140
Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
            195                 200                 205

Lys Ala Lys Lys Ser Gln Leu Thr Leu Asp Lys Phe Phe Lys Lys Pro
        210                 215                 220

<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5
ttgcgaaaga agtaggtatt gag                                              23

<210> SEQ ID NO 6
<211> LENGTH: 25
<212> TYPE: DNA
<213> ORGANISM: Artificial Sequence
<220> FEATURE:
<223> OTHER INFORMATION: Synthetic construct

<400> SEQUENCE: 6
caggattact cgttgattga ataac                                            25

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (10)..(10)
<223> OTHER INFORMATION: ribonucleotide
<220> FEATURE:
<223> OTHER INFORMATION: Synthetic construct

<400> SEQUENCE: 7
acaaccacgg atactttctt caatg                                            25
```

ENRICHMENT OF *LISTERIA* SPP

CROSS-REFERENCE TO RELATED APPLICATIONS

This application claims benefits from U.S. Provisional Patent Application No. 61/378,099, filed on Aug. 30, 2010, the content of which is hereby incorporated by reference in its entirety.

FIELD

One or more embodiments relate to a medium for enriching *Listeria* spp. and an enrichment method of *Listeria* spp.

RELATED ART

*Listeria* spp. bacteria are gram-positive, non-spore forming and motile bacilli and can grow in a wide temperature range of about −4° C. to about 45° C. and a wide pH range of about ≦5.5 to about 9.5. The *Listeria* genus contains six species, including *Listeria monocytogenes, L. innocua, L. welshimeri, L. seeligeri, L. ivanovii,* and *L. grayi*. Among these species of *Listeria, L. monocytogenes* is the cause of most human listeriosis cases. The immunocompromised, pregnant women, elderly, and neonates are susceptible to infection caused by this species. Typical symptoms of listeriosis include septicemia, meningitis and miscarriage.

Consumption of contaminated foods is the major cause of *Listeria* infection. There have been epidemics of various *Listeria*-induced infections caused by the consumption of contaminated foods, such as unpasteurized milk, contaminated cheese, coleslaw, and the like. Therefore, there is an increasing demand for a method of rapid, sensitive, and accurate detection of *Listeria* in a sample, such as in a food, a surface wipe, or medical sample.

An exemplary *Listeria* detection method involves pre-enriching *Listeria* spp. in a enrichment medium and isolating a single colony from a selection medium. The shape and biochemical characteristics of the isolated single colony is analyzed which usually takes 6 to 8 days.

SUMMARY

According to the embodiments, enrichment media which maintain a high growth rate, allow repair of injured cells, and suppress growth of competing species are provided.

One or more embodiments provide a medium to efficiently enhance growth of *Listeria* spp. and the medium is not inhibitory to genetic detection or minimizes genetic detection inhibition.

One or more embodiments provide a method of efficiently cultivating *Listeria* spp. by using the medium.

One or more embodiments provide an efficient method of detecting the presence of *Listeria* spp. in a sample.

In an embodiment, the enrichment medium may include, per 1 L of purified water, about 3 to about 300 g of tryptic soy broth (TSB), about 0.6 to about 60 g of yeast extract (YE), and about 0.5 to about 100 g of lithium chloride.

In an embodiment, the enrichment medium may include, per 1 L of purified water, about 10 to about 90 g of tryptic soy broth (TSB), about 2 to about 18 g of yeast extract (YE), and about 0.1 to about 30 g of lithium chloride.

Still in an embodiment, the enrichment medium may include, per 1 L of purified water, about 10 to about 40 g of tryptic soy broth (TSB), about 1 to about 10 g of yeast extract (YE), and about 1 to about 10 g of lithium chloride.

In am embodiment, the enrichment medium may further contain a beef extract.

BRIEF DESCRIPTION OF DRAWINGS

FIG. 5 is a graph illustrating the recovery of *L. welshimeri*, collected from a contaminated surface of stainless steel, in different media, wherein the curves with solid symbols (-●-, -■-, -▲-) indicate the results with the medium according to the embodiment, and the curves with open symbols (-○-, -□-, -△-) indicate the results with the UVM-1 medium. In FIG. 5, solid circle: *Listeria* enriched in medium A1, surface contaminated at $1\times10^4$ cfu/1 in$^2$; solid triangle: *Listeria* enriched in medium A1, surface contaminated at $1\times10^3$ cfu/1 in$^2$; Solid square: *Listeria* enriched in medium A1, surface contaminated at $1\times10^2$ cfu/1 in$^2$; Open circle: *Listeria* enriched in UVM medium, surface contaminated at $1\times10^4$ cfu/1 in$^2$; Open triangle: *Listeria* enriched in UVM medium, surface contaminated at $1\times10^3$ cfu/1 in$^2$; Open square: *Listeria* enriched in UVM medium, surface contaminated at $1\times10^2$ cfu/1 in$^2$.

DETAILED DESCRIPTION

According to embodiments, the enrichment medium maintains a high growth rate, allows repair of injured cells, and suppresses growth of competing species. The growth rate is high enough for *Listeria* spp. to be detectable within a short time. Furthermore, the medium does not interfere or inhibit a genetic detection of enriched *Listeria* spp., for example, by a polymerase chain reaction (PCR).

In an embodiment, the enrichment medium may include, per 1 L of purified water, about 3 to about 300 g of tryptic soy broth (TSB), about 0.6 to about 60 g of yeast extract (YE), and about 0.5 to about 100 g of lithium chloride.

In an embodiment, the enrichment medium may include, per 1 L of purified water, about 10 to about 90 g of tryptic soy broth (TSB), about 2 to about 18 g of yeast extract (YE), and about 0.1 to about 30 g of lithium chloride.

Still in an embodiment, the enrichment medium may include, per 1 L of purified water, about 10 to about 40 g of tryptic soy broth (TSB), about 1 to about 10 g of yeast extract (YE), and about 1 to about 10 g of lithium chloride.

Throughout the disclosure, the amounts of the ingredients are intended to be based on 1 L of water or other available types of medium base, unless indicated otherwise.

The TSB may be a soybean-casein digest medium. The TSB may be commercially available from, for example, DIFCO™ Laboratories Inc., and ACUMEDIA™ Inc. For example, the TSB may contain enzymatic digests of casein and soybean meal. The enzyme may be papain or pancreatic enzymes. For example, the TSB may contain, per 1 L of distilled water, about 17 g of BACTO™ tryptone, which is a pancreatic digest of casein, about 3 g of BACTO™ soytone, which is a papain digest of soybean meal, about 2.5 g of BACTO™ dextrose, about 5 g of sodium chloride, and about 2.5 g of dipotassium phosphate. The enzymatic digests of casein and soy meal serve as nitrogen sources, and dextrose is a carbon source facilitating the growth of the microorganism. Casein is a main milk protein and is a rich source of amino acid nitrogen. Sodium chloride maintains osmotic pressure balance, and dipotassium phosphate is a buffering agent. For rehydration, about 30 g of the TSB may be suspended in 1 L of purified water with slight warming to completely dissolve. Then, a desired amount of the TSB is subjected to sterilization, for example, by filtration or by using an autoclave at 121° C. for 15 minutes.

The yeast extract (YE) may be yeast autolysate or yeast hydrolysate. For example, the YE may include the water-soluble compounds of yeast autolysate. In this regard autolysis of the yeast cells may be carefully controlled to preserve natural vitamin B complexes. The YE may be obtainable by growing *Saccharomyces* spp. in carbohydrate-rich plant media. The yeast may be harvested, washed and resuspended in the water, and then self-digested with its own enzymes ("autolysis") in the water. The autolytic activities of the enzymes may be lost by heating. The resulting YE is filtered until it becomes clear, and the filtrate is spray-dried into powder form. The YE may supply vitamins, nitrogen, amino acids, and carbon to the medium. The YE may be commercially available from, for example, DIFCO™ Laboratories Inc., and ACUMEDIA™ Inc.

Inventors found that the presence of lithium chloride in the medium suppresses growth of competing bacteria such as *Enterococcus* spp. and *Bacillus* spp.

The enrichment medium may further contain at least one component selected from the group consisting of about 0.5 to about 50 g of beef extract (BE), or a vitamin mix containing about 0.01 to about 1 mg of riboflavine, about 0.1 to about 10 mg of thiamine, and about 0.1 to about 10 mg of biotin; about 0.2 to about 20 g of pyruvate or a salt thereof; and about 0.01 to about 1 g of ferric ammonium citrate.

The enrichment medium may further contain at least one component selected from the group consisting of about 1 to about 10 g of beef extract (BE), or a vitamin mix containing about 0.01 to about 0.5 mg of riboflavine, about 0.5 to about 1.5 mg of thiamine, and about 0.01 to about 1.5 mg of biotin; about 1 to about 5 g of pyruvate or a salt thereof; and about 0.01 to about 1 g of ferric ammonium citrate.

The beef extract (BE) is derived from beef infusion and is an undefined source of nutrients. The BE is not subjected to harsh treatment for protein hydrolysis, and thus may supplement some nutrients lost during the production of peptones. The BE is a mixture of amino acids, nucleotide fragments, organic acids, minerals, and some vitamins. The BE may facilitate amplification of target nucleic acids during the PCR using the culture product as template. In addition, the BE may also facilitate recovery of sub-lethally heat-injured *Listeria* spp. The BE may be replaced with a vitamin mix containing about 0.01 to about 0.5 mg of riboflavine, about 0.5 to about 1.5 mg of thiamine, and about 0.01 to about 1.5 mg of biotin.

Pyruvate or a salt thereof that are suitable for use in the enrichment medium may be sodium pyruvate. Pyruvate may facilitate recovery of sub-lethally heat-injured *Listeria* spp.

Ferric ammonium citrate may serve as a growth enhancer for *Listeria* spp. Ferric ammonium citrate may be used in an amount of about 0.01 g to about 1 g. For example, about 0.025 g to about 0.075 g of ferric ammonium citrate may be used. For example, about 0.05 g of ferric ammonium citrate may be used.

The medium may further contain a buffer compound. The buffer compound may be a compound that does not inhibit detection of target nucleic acids from the culture product by PCR amplification. The buffer compound may include, for example, 3-(N-morpholino)propanesulfonic acid (MOPS) free acid and a sodium salt thereof. The MOPS free acid may be used in an amount that is appropriate to maintain pH of the medium between 7.0 and 8.0. The buffer compound may contain about 0.4 g to about 40 g of the MOPS free acid and about 0.7 g to about 70 g of sodium MOPS. In an embodiment, the buffer compound may contain about 2-8 g of MOPS free acid and about 3.0-15 g of sodium MOPS. For example, the buffer compound may contain about 4 g of MOPS free acid and about 7.1 g of sodium MOPS.

The medium may contain an antibiotic for selectively facilitating growth of *Listeria* spp. The antibiotic may be selected from the group consisting of about 1 to about 10 mg of acriflavine, about 5 to about 15 mg of polymyxin B, and about 10 to about 30 mg of ceftazidime. For example, the antibiotic may be a mixture of about 1 to about 10 mg of acriflavine, about 5 to about 15 mg of polymyxin B, and about 10 to about 30 mg of ceftazidime.

The medium may be in any form selected from dried powder form, paste form, and liquid form. The medium may not contain esculin. Esculin (6-(beta-D-glucopyranosyloxy)-7-hydroxy-2H-1-benzopyran-2-one, CAS No. 531-75-9) is a kind of glucoside and is a fine blue fluorescent color. However, as long as the concentration of esculin is low enough not to interfere with PCR reaction, esculin may exist in the medium.

In an embodiment, the enrichment medium may contain, per 1 L of purified water, about 10 to about 40 g of tryptic soy broth (TSB), about 1 to about 10 g of yeast extract (YE), about 1 to about 10 g of lithium chloride; about 1 to about 10 g of beef extract (BE) or a vitamin mix containing about 0.01 to about 0.5 mg of riboflavine, about 0.5 to about 1.5 mg of thiamine, and about 0.01 to about 1.5 mg of biotin; about 1 to about 5 g of pyruvate or a salt thereof; about 0.05 to about 0.5 g of ferric ammonium citrate; about 1-8 g of MOPS free acid and about 2-14 g of sodium MOPS; and about 1 to about 10 mg of acriflavine, about 5 to about 15 mg of polymyxin B, and about 10 to about 30 mg of ceftazidime.

The ratio between TSB and yeast extract may be in a range from 1:0.05-0.5 by wt or from 1:0.1-0.3 by wt. The ratio between TSB and beef extract may be in a range from 1:0.05-0.5 by wt or from 1:0.1-0.2 by wt. The ratio between TSB and pyruvate may be in a range from 1:0.01-0.2 by wt or from 1:0.05-0.1 by wt. The ratio between TSB and MOPS (in free acid form) may be in a range from 1:0.05-0.5 by wt or from 1:0.1-0.2 by wt. The ratio between TSB and MOPS (in salt form) may be in a range from 1:0.05-0.7 by wt or from 1:0.1-0.4 by wt. The ratio between TSB and lithium chloride may be in a range from 1:0.1-0.8 by wt or from 1:0.2-0.5 by wt. In one embodiment, the ratios between TSB:yeast extract:beef extract:pyruvate:MOPS (free acid):MOPS (in salt form): lithium chloride is 1:0.2:0.16-0.17:0.06-0.07:0.13-0.14:0.2-0.3:0.3-0.4 by wt.

For example, the enrichment medium may contain, per 1 L of purified water, about 30 g of tryptic soy broth (TSB), about 6 g of yeast extract (YE), about 1 to about 10 g of lithium chloride; about 5 g of beef extract (BE) or a vitamin mix containing about 0.1 mg of riboflavine, about 1 mg of thiamine, and about 1 mg of biotin; about 2 g of sodium pyruvate;

about 0.2 g of ferric ammonium citrate; about 4 g of MOPS free acid and about 7.1 g of sodium MOPS; and about 5 mg of acriflavine, about 10 mg of polymyxin B, and about 20 mg of ceftazidime.

According to embodiments, a method of enriching *Listeria* spp. in a sample includes cultivating the sample including *Listeria* spp. in the enrichment medium described above.

The cultivating may be conducted using any method known in the art to be suitable for cultivating *Listeria* spp. For example, the cultivating may be conducted at a temperature of about −4° C. to about 35° C. For example, the cultivating may be conducted at a temperature ranging from room temperature to about 37° C. For example, the cultivating may be conducted at a temperature of about 22° C. to about 30° C. The cultivation time may also be appropriately varied depending on the purpose of analysis. The cultivation time may be, for example, in a range of 6 hours to 6 days. For example, the cultivation time may be from 6 hours to 24 hours. The medium used herein is as described above. The sample containing *Listeria* spp. may be inoculated directly into the medium or may be collected on swab or sponge. A wet sponge or wet swab may be used to collect microorganisms and move them into a container. Then, the growth medium may be added into the container, mixed by, for example vortexing for 10 seconds, and incubated at a temperature of about 30 to about 37° C.

According to embodiments, a method of detecting the presence of *Listeria* spp. in a sample includes: culturing a sample including *Listeria* spp. in the enrichment medium to obtain a culture; conducting a PCR using the culture as template and primers specific to *Listeria* spp. to obtain PCR products; and determining the presence of *Listeria* spp. in the sample based on the PCR products. Hereinafter, the method will now be described in greater detail.

The method involves culturing a sample including *Listeria* spp. in the enrichment medium. This step is as described above.

The method may involve conducting PCR using the culture as template and primers specific to *Listeria* spp. The template may be selected from among the culture products, pellets obtained by centrifuging the culture products, and nucleic acid isolates from the culture products. The primers specific to *Listeria* spp. may be capable of specifically binding to ribosome RNA, for example, 16S or 23S rRNA, or a certain gene such as prs gene of *Listeria* spp. Examples of *Listeria* spp. strains may include, but are not limited to, *L. monocytogenes, L. ivanovii, L. grayi, L. welshimeri, L. seelgrei,* and *L. innocua*.

The PCR may be any known PCR method. In an embodiment, the PCR may be conducted in the presence of forward and reserve primers capable of specifically binding to target nucleic acids, a CATACLEAVE™ probe having a chimeric structure comprised of a DNA sequence and an RNA sequence, and a RNase H capable of cleaving a DNA and RNA duplex. In an embodiment, the CATACLEAVE™ probe may have a structure of DNA-RNA-DNA (in a direction of 5'->3') and its 5'- and 3'-ends may be labeled with a FRET pair. The CATACLEAVE™ probe may be hybridized to a target nucleic acid. The PCR products may be measured in real time by detecting signals from the cleavage sites of the RNase H from the hybrid of target nucleic acids or amplified products and the CATACLEAVE™ probe.

The PCR may be real-time PCR developed to monitor amplification during the PCR process. This real-time PCR may employ fluorescently labeled probes that bind to the newly synthesized DNA, or dyes whose fluorescent emission is increased when intercalated into double stranded DNA. The probes are generally designed so that donor emission is quenched when no cleavage occurs to the probe by fluorescence resonance energy transfer (FRET) between two chromophores. A donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Examples of donor chromophores include FAM, TAMRA, VIC, JOE, Cy3, Cy5, and Texas Red. Acceptor chromophores are chosen so that their excitation spectra overlap with the emission spectrum of the donor. An example of such a pair is FAM-TAMRA. In addition, an example of the detectable label is a non-fluorescent acceptor that will quench a wide range of donors. Other examples of appropriate donor-acceptor FRET pairs will be known to those of skill in the art. An example of FRET probes is CATACLEAVE™ probes. Examples of CATACLEAVE™ probes are disclosed in U.S. Pat. No. 5,763,181, of which content is incorporated herein by reference. When CATACLEAVE™ probes are cleaved, donor and acceptor chromophores are sufficiently separated from each other, thereby suppressing FRET. Cleavage of CATACLEAVE™ probes may be achieved by a second enzyme that does not have polymerase activity. CATACLEAVE™ probes may have a target sequence of an endonuclease, such as a restriction enzyme or RNase, within their molecule.

The PCR reaction mixture includes a RNase H enzyme that will specifically cleave the RNA sequence portion of a RNA-DNA duplex. After cleavage, the two halves of the probe dissociate from the target amplicon at reaction temperature and diffuse into the reaction buffer. As the donor and acceptors separate FRET is reversed and donor emission can be monitored. Cleavage and dissociation regenerates a site for further CATACLEAVE™ probe binding. In this way it is possible for a single amplicon to serve as a target or multiple rounds of probe cleavage until the primer is extended through the CATACLEAVE™ probe binding site. The RNase H may be thermostable.

For example, the PCR may be conducted in the presence of a forward primer of SEQ ID NO. 1 (TCCAAGCAGTGAGT-GTGAGAA), a reverse primer of SEQ ID NO. 2 (TGA-CAGCGTGAAATCAGGA), a labeled CATACLEAVE™ probe of SEQ ID NO. 3 (CCATCACAGCTCArUGCT-TCGC), and the RNase H. The ends of the CATACLEAVE™ probe may be labeled with a FRET pair. In addition, the primers may be specific to a species of *Listeria* spp. The RNase H may have an amino acid sequence of SEQ ID NO. 4. For example, the PCR may be conducted in the presence of a forward primer of SEQ ID NO. 5 (ACGAGTAACGGGA-CAAATGC), a reverse primer of SEQ ID NO. 6 (TC-CCTAATCTATCCGCCTGA), a labeled CATACLEAVE™ probe of SEQ ID NO. 7 (CGAATGTAArCAGACACG-GTCTCA), and the RNase H. The sequences of SEQ ID NOs. 5, 6 and 7 may specifically bind to the internalin A gene of *L. monocytogenes*. In another embodiment, the PCR may be conducted in the presence of primer of SEQ ID NO: 5 and the probe of SEQ ID 7, or in the presence of primer of SEQ ID NO: 6 and the probe of SEQ ID NO: 7.

RNase H may hydrolyze RNA in the RNA-DNA hybrid. For RNase H activity, a divalent ion (for example, $Mg^{2+}$, $Mn^{2+}$) is required. The RNase H cleaves RNA 3'-O—P linkages to produce 3'-hydroxyl and 5'-phosphate end products. Examples of the RNase H include *Pyrococcus furiosus* RNase HII, *Pyrococcus horikoshi* RNase HII, *Thermococcus litoralis* RNase HI, and *Thermus thermophilus* RNase HI.

The RNase H may be thermostable. Additional examples of RNase H enzymes and hot start RNase H enzymes that can be employed in the invention are described in U.S. Patent Application No. 2009/0325169 to Walder et al., the content of which is incorporated herein in its entirety.

The RNase H may be reversibly modified to couple to an inhibiting factor, so that it becomes inactive as an endonuclease. The release of the inhibiting factor from the RNase H may reactivate enzymatic activity. The inhibiting factor may be a ligand or a reversible chemical reaction. Examples of the reversible chemical reaction may be crosslinking of the RNase H and acylation of a specific residue of the RNase H. The release of the inhibiting factor from the RNase H may be achieved by heating the sample containing inactive RNase H to a temperature of about 90° C., for example, to a temperature of about 95° C., and/or by lowering the pH of the sample to about 7.0 or less. The crosslinking may be achieved by using formaldehyde.

Using the enrichment medium according to embodiments, the growth of Listeria spp. may be selectively or nonselectively enhanced, and may be detected without interfering PCR.

Using the method of enhancing the growth of Listeria spp. in a sample according to embodiments, the growth of Listeria spp. may be selectively or nonselectively enhanced.

Using the method of enhancing the growth of Listeria spp. in a sample according to embodiments, the presence of Listeria spp. in the sample may be detected at high specificity and high sensitivity.

The present invention will be described in further detail with reference to the following examples. These examples are for illustrative purposes only and are not intended to limit the scope of the invention.

EXAMPLE 1

Selection of Minimal Medium

A medium enhancing the growth of Listeria spp. during culture for 24 hours and which prevents or minimizes the inhibition of Listeria spp. detection caused by PCR was chosen.

Most commercially available Listeria spp.-enhancement media include high content of salt since Listeria have high osmolarity tolerance. For example, any salt selected from NaCl, and selection salt (LiCl) may be used in an amount of about 15 to about 20 g.

For comparison, Fraser broth (5 g of proteose peptone, 5 g of tryptone/casein dig., 5 g of beef extract (BE), 5 g of yeast extract (YE), 20 g of NaCl, 12 g of $Na_2HPO_4.2H_2O$, 1.35 g of $KH_2PO_4$, 1 g of esculin, 0.5 g of iron (III) $NH_4$ citrate, 3 g of LiCl, 0.024 g of acroflavine HCl, 0.02 g of nalidixic acid) was used, and PCR was conducted using the primers of SEQ ID NO: 5, 6, and the probe of SEQ ID NO: 7.

Culture was subjected to lysis and the lysate was subjected to PCR reaction. As a result, the Fraser broth completely inhibited the PCR.

Minimal media A, A1 and B having the compositions below were prepared.

Composition of Minimal Medium A (Per 1 L of Distilled Water):

| Ingredient | Concentration (g/L) |
|---|---|
| TSB | 30 |
| Yeast extract | 6 |
| Ferric ammonium citrate | 0.1 |
| LiCl | 3 |
| Esculin | 1 |

Composition of Minimal Medium A1 (Per 1 L of Distilled Water):

| Ingredient | Concentration (g/L) |
|---|---|
| TSB | 30 |
| Yeast extract | 6 |
| Ferric ammonium citrate | 0.1 |
| LiCl | 3 |

Composition of Minimal Medium B (Per 1 L of Distilled Water):

| Ingredient | Concentration (g/L) |
|---|---|
| TSB | 30 |
| Peptone | 5 |
| Yeast extract | 6 |
| Ferric ammonium citrate | 0.1 |
| LiCl | 3 |

In preparation of these media, after weighing out medium ingredients, distilled water was added to the medium ingredients, and the medium ingredients were sterilized by autoclave at 121° C. for 15 minutes. No antibiotic was added to the media. OXOID ONE BROTH™-Listeria and DUPONT™ 24-hr Listeria Broth, which are commercially available 24-hr enrichment media, were used as control groups. Compositions of these media are not available to public as manufacturer's propriety information.

300 µL of overnight cultures (about of $3 \times 10^9$ CFU/ml) of Listeria monocytogenes in a brain hear infusion (BHI) medium was added into 30 mL of each of the pre-warmed media in 250 ml glass flask. Each mixture was cultured without shaking at 35° C. for 24 hours. Aliquots (20 µL) of the culture products were collected from each container after culture for 1, 2, 3, 4, 5, 6, 7, 8, 9 and 24 hours, respectively. Each culture product was treated with a TZ lysis buffer with 1 mg/ml proteinase K, and incubated at 55° C. for 15 min, 95° C. for 10 min, and cooled at 4° C. for 2 min. Cell lysates were added into the PCR mixture for real-time PCR. The PCR mixture contained forward and reverse primers of SEQ ID NOs. 5 and 6, the probe of SEQ ID No. 7, and the RNase H. The primers and probe were specific to the InlA gene of L. monocytogenes. The 5' and 3' ends of the probe were labeled with FAM and Iowa BFQ (Black Hole Quencher), respectively.

The PCR conditions were as follows: UNG activation at 37° C. for 600 seconds; Denaturation at 95° C. for 600 seconds; Denaturation at 95° C. for 15 seconds; and annealing and elongation at 60° C. for 20 seconds (50 cycles). The composition of the PCR mixture per well was as follows: 2.5 µl of 10× ICAN (320 mM HEPES (pH 7.8, titrated by concentrated KOH), 40 mM magnesium acetate, 1000 mM potassium acetate, 10% DMSO, 1.1% BSA), 1 µL of forward primer of SEQ ID NO: 5 (20 pm/µL), 1 µL of reverse primer of SEQ ID NO: 5 (20 pm/μL), 1 μL of probe of SEQ ID NO: 7 (5 pm/μL), 1 μL of dNTP/dUTP (2/4 mM) (Fermentas), 0.5 μL of 5 u/μL Taq polymerase, 0.1 μL of 10 u/μL UNG, 0.2 μL of 5 u/μL RNase H, 2 μL of culture lysate (DNA), and 15.7 μL of water.

Figure 1A:
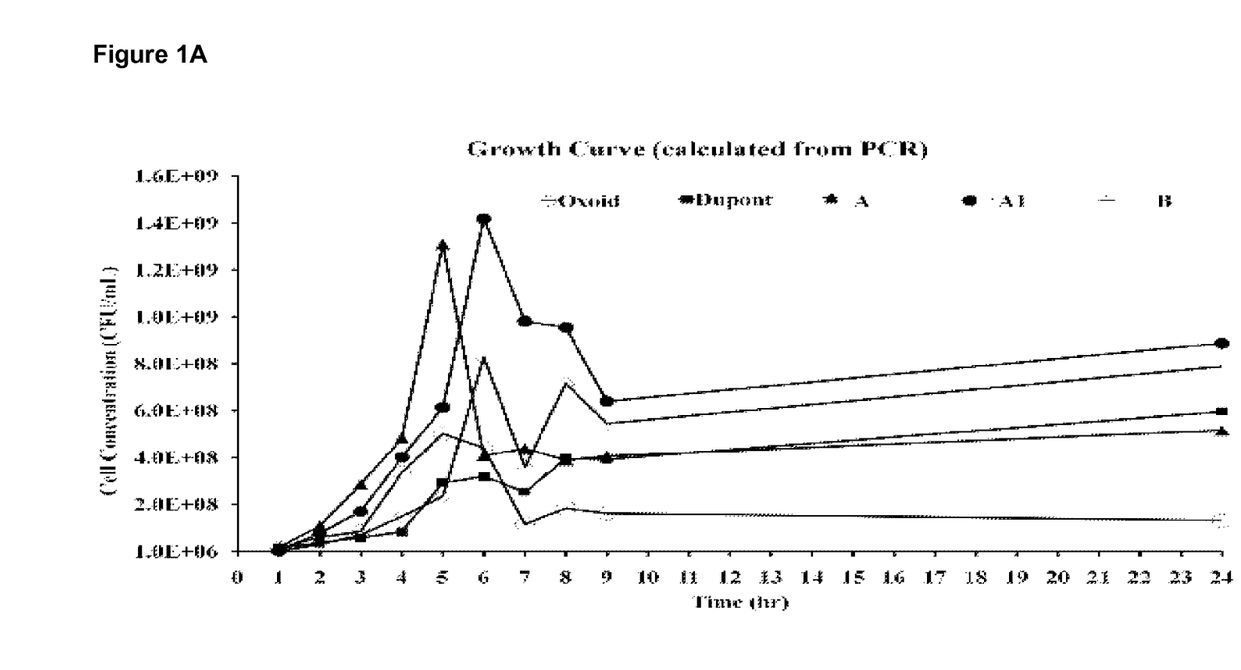
FIG. 1A is a graph illustrating cell concentrations in different media with respect to time, calculated from a polymerase chain reaction (PCR)

FIG. 1A is a graph illustrating cell concentrations in different media with respect to time, calculated from a PCR. Referring to FIG. 1A, no inhibition to PCR was found in the OXOID ONEBROTH™ medium.

In addition, following experiments were conducted: Overnight-grown *Listeria monocytogenes* was diluted with 0.5% non-fat milk to 27 cfu/100 uL. Each 1 in² of ceramic tile surface was contaminated by 100 μL, suspension, and air-dried overnight. Contaminated surfaces were wiped by cotton swabs which were then incubated either in medium A1 or UVM medium at 35° C. or 30° C. for 24 hours.

Out of 10 replicates, 7 were positive in medium A1 with an average Cp value of 22.9. Only 4 out of 10 were positive in UVM medium with an average Cp of 39.5. Results are shown in FIG. 1(B).

Figure 1B:
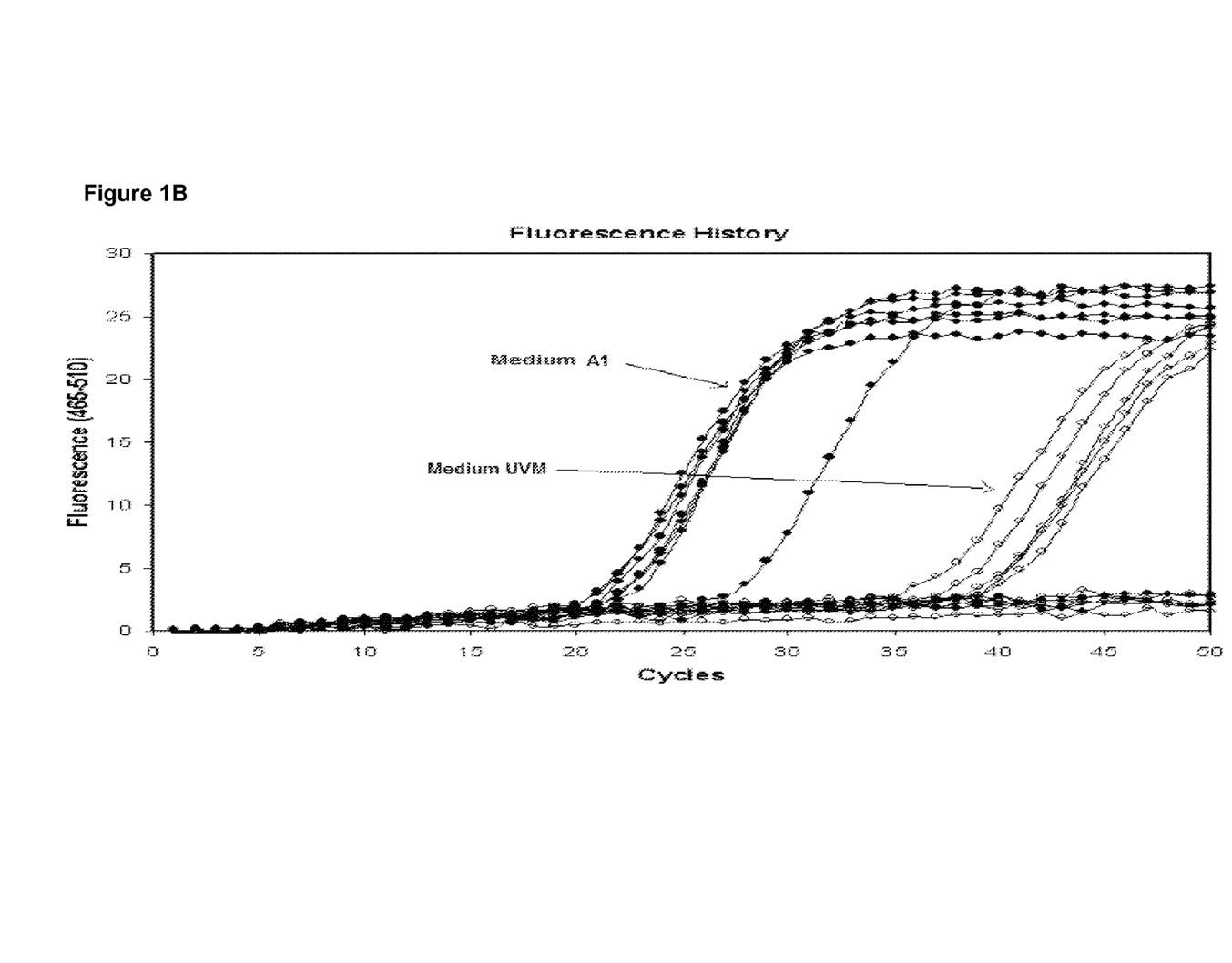
FIG. 1B shows amplification graphs for the PCT results with A1 medium and UVM-1 medium.

FIG. 1(B) is graphs showing PCR results using optimized Medium A1 and using UVM. Solid circles are Optimized Medium A1 and open circles are UVM medium.

Optimized Medium A1, employed for this test, had the following composition:

| Basal Medium | | | |
|---|---|---|---|
| Components (Basal) | Concentration (g/L) | Supplements (mg/L) | |
| TSB | 30 | Acriflvaine | 5 |
| Yeast extract | 6 | Polymyxin B | 10 |
| Beef extract | 5 | Ceftazidime | 20 |
| Sodium pyruvate | 2 | Riboflavin | 0.1 |
| MOPS, free acid | 4 | Thiamine | 1 |
| MOPS, sodium salt | 7.1 | Biotin | 1 |
| Lithium chloride | 10 | | |
| Ferric ammonium citrate | 0.1 | | |

EXAMPLE 2

Selection of Medium

Individual ingredients of the Minimal Medium A1 selected in Example 1 that may have effects of enhancing the growth of *Listeria* spp. were identified and investigated.

(1) Concentration of Lithium Chloride

By following the same procedure in Example 1 using Minimal Medium A1 as a base medium, LiCl was added to the basal medium to a concentration of 1, 3, 5, 7, 9 or 10 g/L. At the range between 7 and 10 g/L, the Cp values were very similar, indicating high LiCl concentration helped recovery of *Listeria*.

Figure 2:
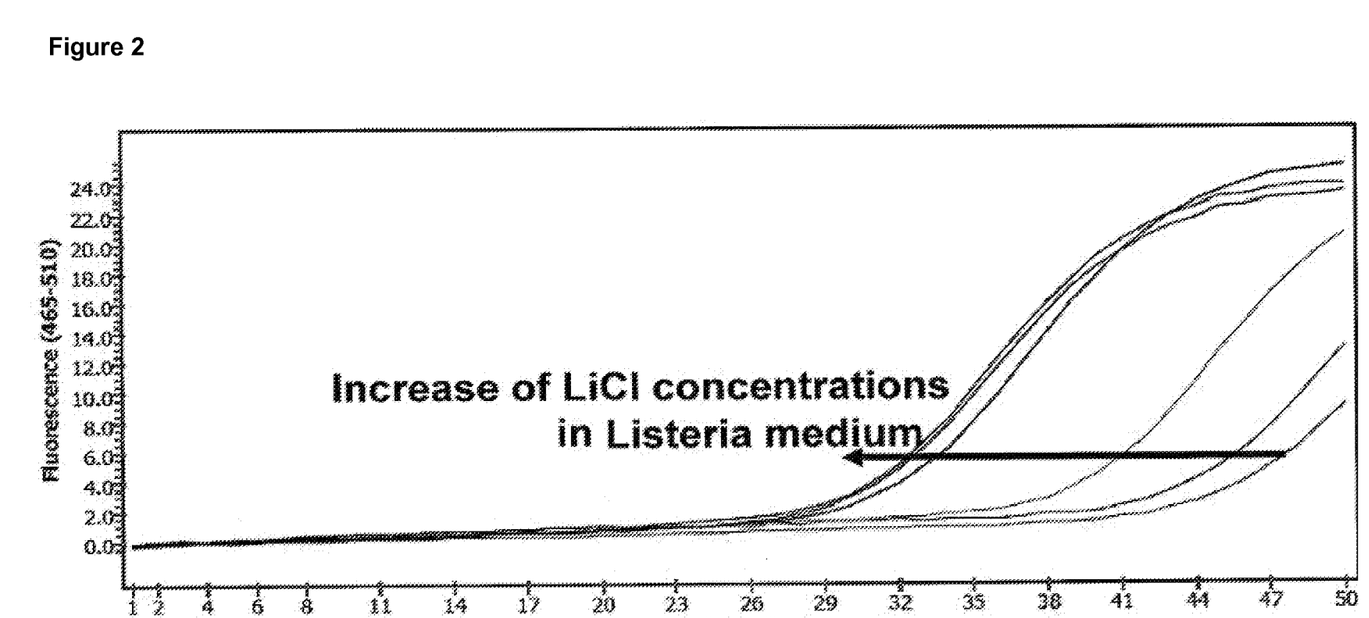
FIG. 2 is a graph of PCR results with the Minimal Medium A1, illustrating a change in cell concentration with respect to a concentration of LiCl in the Minimal Medium A1.

FIG. 2 is a graph of PCR results with the Minimal Medium A1, illustrating a change in cell concentration with respect to a concentration of LiCl in the Minimal Medium A1. Referring to FIG. 2, the higher the concentration of LiCl, for example in the range of 1-10 g/L, the smaller the Cp values and the more the cell growth was enhanced.

(2) Culture of *Listeria* spp. in the Presence of Antibiotic

Sixty *L. monocytogenes* strains were cultured at 35° C. in the Minimal Medium A1 supplemented with antibiotics (10 mg/L of acriflavine, 40 mg/L of nalidixic acid, 10 mg/L of polymyxin B, and 40 mg/L of ceftazidime). As a result, all the strains reached to maximum densities after overnight culture.

Separately, five *L. grayi* strains were cultured at 35° C. in the Minimal Media A1 supplemented separately with 10 mg/L of acriflavine, 40 mg/L of nalidixic acid, 10 mg/L of polymyxin B, 40 mg/L of ceftazidime, and a combination thereof. As a result, the effects of each antibiotic on the growth of *L. grayi* were trivial. However, growth retardation was observed in two of the *L. grayi* strains when all the antibiotics were used. The two strains reached maximum cell densities within about 24 hours.

Figure 3:
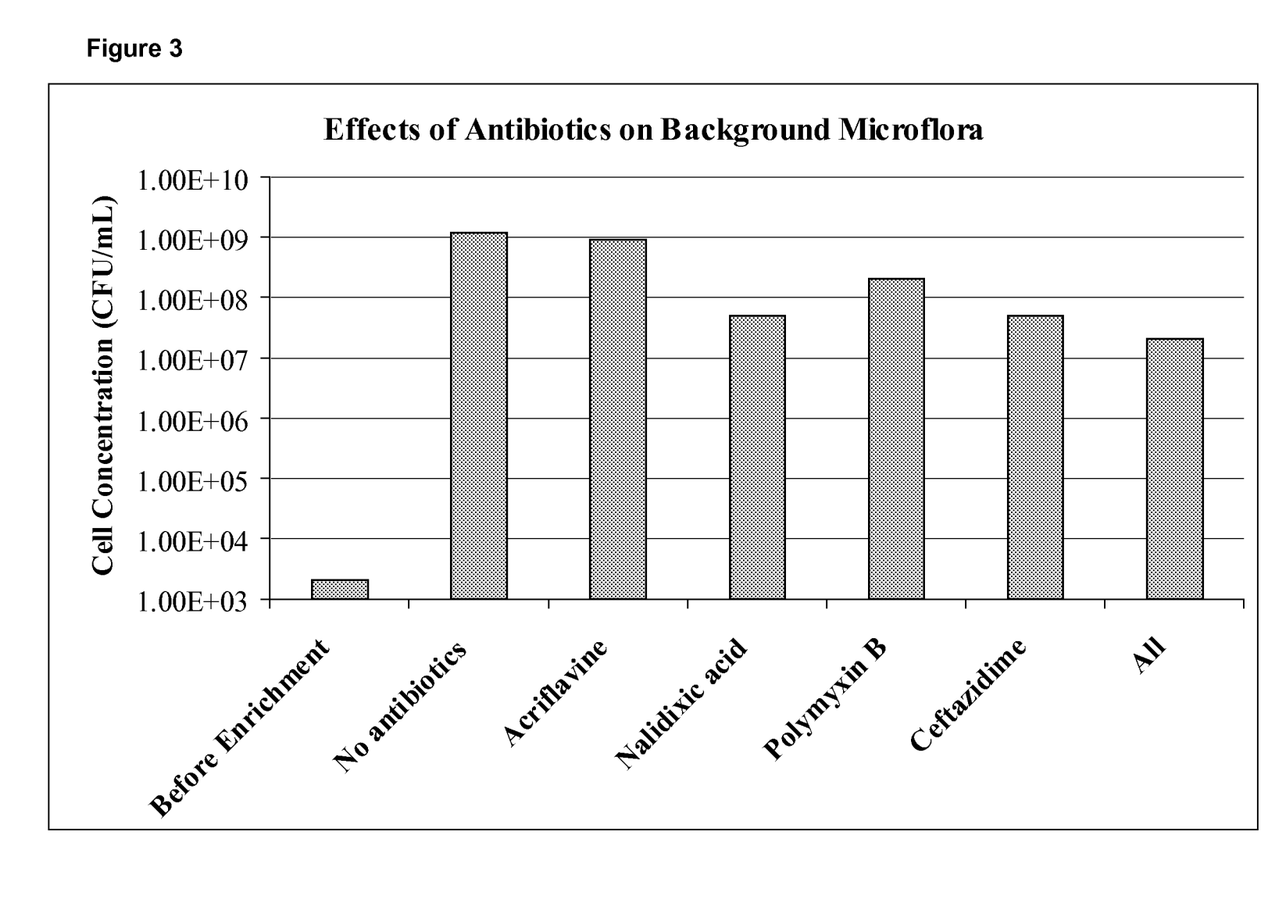
FIG. 3 is a graph illustrating the effects of antibiotics on background microflora.

In addition, effects of antibiotics on background microflora were investigated. First, 10 g/L of ground beef was cultured at 35° C. in the Minimal Media A supplemented separately with 10 mg/L of acriflavine, 40 mg/L of nalidixic acid, 10 mg/L of polymyxin B, 40 mg/L of ceftazidime, and a combination thereof. The cell concentrations before and after culture were determined based on aerobic plate counts. The aerobic plate counts were determined by inoculating 100 μL of the culture products into DIFCO™ Plate Count agar medium, culturing the mixture at 35° C. for 24 hours, and counting cell colonies FIG. 3 is a graph illustrating the effects of antibiotics on background microflora. Referring to FIG. 3, the growth of the background microfluora was inhibited about 100 times more strongly when the four antibiotics were added together, than when they were used individually. In addition, nalidixic acid among the four antibiotics showed the strongest inhibitory effect on cell growth.

(3) Recovery of Heat-injured *Listeria* Cells

Most *Listeria* infection cases are associated with pasteurized dairy products. Therefore, the effects of the Minimal Medium A1 on the recovery of sub-lethally heat-injured *Listeria* spp. were investigated. Overnight-cultured *Listeria monocytogenes* was serially diluted by 10 folds with PBS. 1 mL of the culture suspension (about 3780 CFU) was cultured at 50° C. for 10 minutes, and 0.1 mL of the culture product was inoculated on the Minimal Medium A1 in agar plate (1.5% agar) in the presence or non-presence of selective agents.

Figure 4:
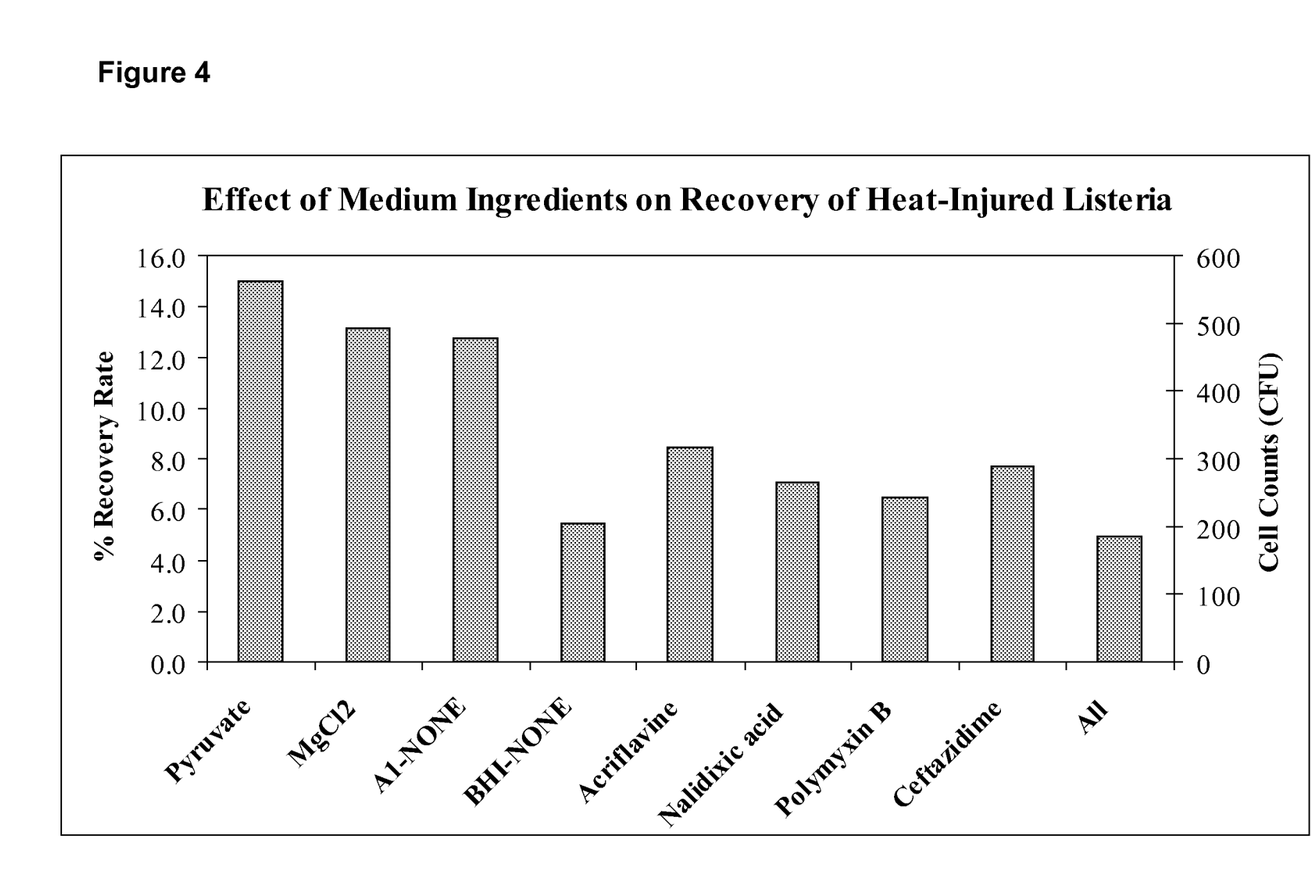
FIG. 4 is a graph illustrating the effects of medium ingredients on the recovery of heat-injured *Listeria* spp.

FIG. 4 is a graph illustrating the effects of medium ingredients on the recovery of heat-injured *Listeria* spp. Referring to FIG. 4, the recovery rate was improved when 10 g/L of sodium pyruvate was used as compared to when 10 mM of MgCl₂ was used. In FIG. 4, "Pyruvate" indicates a Minimal Medium A1 supplemented with sodium pyruvate, "A1-NONE" indicates a Minimal Medium A1 supplemented with none, and "BHI-NONE" indicates a brain heart infusion medium supplemented with none. "Acriflavine," "Nalidixic acid," "Polymyxin B," "Ceftazidime" and "All" denote Minimal Media A supplemented with 10 mg of acriflavine, 40 mg/L of nalidixic acid, 10 mg/L of polymyxin B, 40 mg/L of ceftazidime, and all of these antibiotics, respectively.

Pyruvate, and three other agents, i.e., Acriflavine, Polymyxin B, and Ceftazidime showed positive effects in recovering heat-injured *Listeria* spp.

EXAMPLE 3

Recovery of *Listeria* spp. Collected from Stainless Steel Surface

Overnight-cultured *L. welshimeri* was diluted by 10-fold with 4% non-fat dry milk. 100 μL of the cell suspension was inoculated on a 1-in² stainless steel surface and air-dried overnight. Next, cells were collected with a phosphate buffered saline (PBS)-soaked cotton swab, and cultured at 30° C. for 24 hours in the medium optimized A1 as shown above or a UVM-1 medium (Per 1 liter of water, 5 g of proteose peptone, 5 g of tryptone/casein dig., 5 g of beef extract (BE), 5 g of yeast extract (YE), 20 g of NaCl, 9.6 g of $Na_2HPO_4.2H_2O$, 1.35 g of $KH_2PO_4$, 1 g of esculin, 0.012 g of acroflavine, and 0.02 g of nalidixic acid). The experiment was conducted at three contamination concentrations, i.e., about $1\times10^2$ cfu/$in^2$, about $1\times10^3$ cfu/$in^2$, and about $1\times10^4$ cfu/$in^2$.

Figure 5:
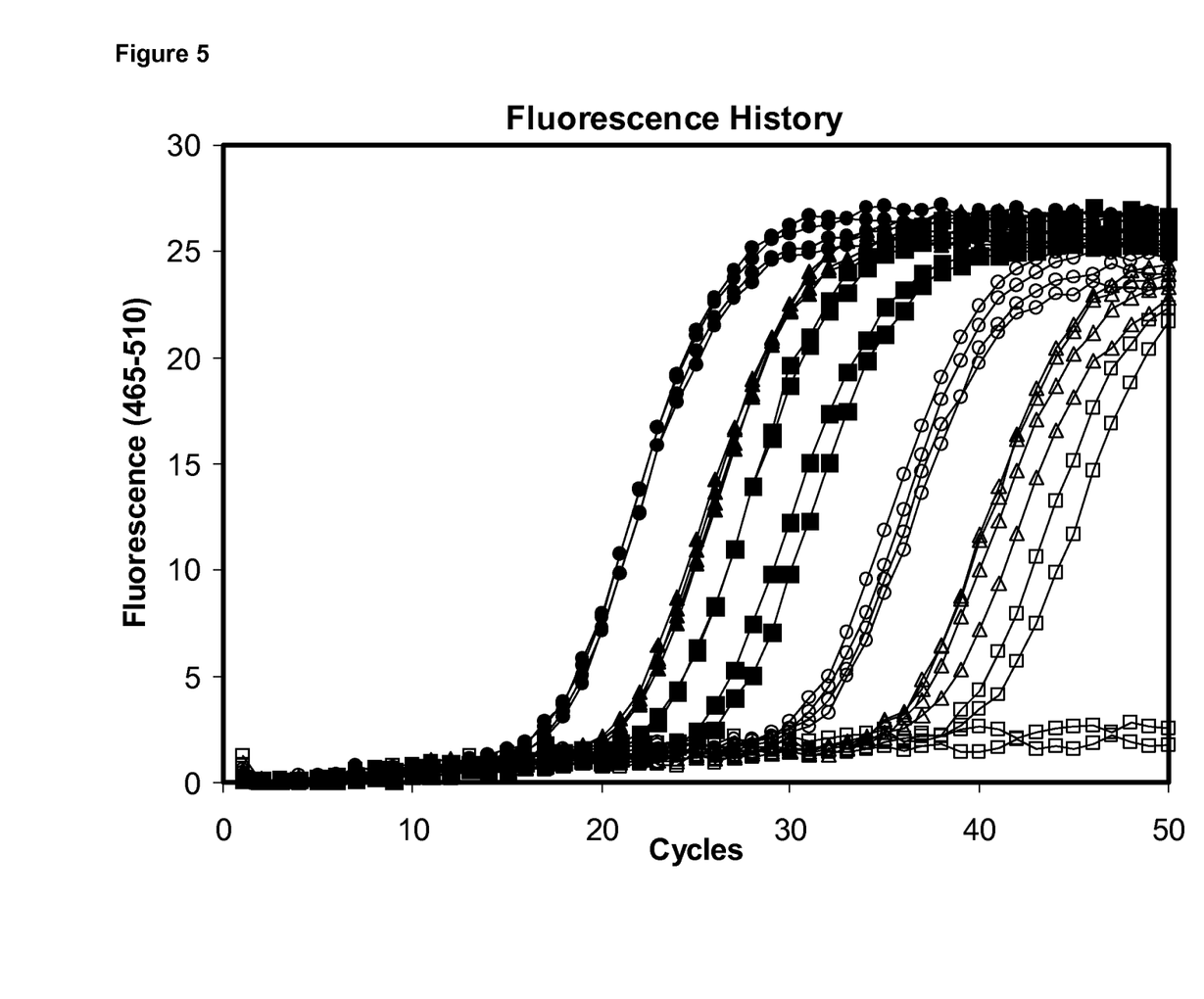

FIG. 5 is a graph illustrating the recovery of L. welshimeri, collected from a contaminated surface of stainless steel, in different media. In FIG. 5, the curves with solid symbols (-●-, -■-, -▲-) indicate the results with the medium A1 according to the embodiment, and the curves with open symbols (-o-, -□-, -Δ-) indicate the results with the UVM-1 medium. In FIG. 5, solid circle: Listeria enriched in medium A1, surface contaminated at $1\times10^4$ cfu/1 $in^2$; solid triangle: Listeria enriched in medium A1, surface contaminated at $1\times10^3$ cfu/1 $in^2$; Solid square: Listeria enriched in medium A1, surface contaminated at $1\times10^2$ cfu/1 $in^2$; Open circle: Listeria enriched in UVM medium, surface contaminated at $1\times10^4$ cfu/1 $in^2$; Open triangle: Listeria enriched in UVM medium, surface contaminated at $1\times10^3$ cfu/1 $in^2$; Open square: Listeria enriched in UVM medium, surface contaminated at $1\times10^2$ cfu/1 $in^2$. Referring to FIG. 5, medium A1 showed better recovery capabilities than the UVM-1 media. The cells were recovered 100% using the media according to embodiments at every contamination concentration. However, just 50% of the cells were recovered using the UVM-1 medium at a contamination concentration of 100 cfu/$in^2$. A faster growth rate was also observed in the medium according to embodiments as indicated by smaller Cp values.

EXAMPLE 4

Effect of MOPS Buffer on the Growth of Listeria spp.

A 3-(N-morpholino)propanesulfonic acid (MOPS) buffer was added into a medium prepared by supplementing the Minimal Medium A1 with 2 g/L of sodium pyruvate (hereinafter, "Medium A2"), and Listeria spp. was cultured in the Medium A2.

(1) Effect of MOPS Buffer

First, sixteen samples, each of 1.5 g ground beef, were inoculated with L. monocytogenes. The samples were cultured at 4° C. overnight. The samples were respectively added into Medium A2 or MOPS-added Medium A2 (100 mM MOPS, pH 7.4), and cultured at 30° C. for 24 hours to enrich L. monocytogenes, resulting in eight replicate samples for each type of medium. The enriched samples were treated with a TZ lysis buffer containing proteinase K to lyse the cells, and cell lysates were analyzed using a forward primer of SEQ NO: 5, a reverse primer of SEQ ID NO: 6, a probe of SEQ ID NO: 7, and an RNase H for L. monocytogenes detection. The PCR conditions were the same as in Example 1.

Figure 6:
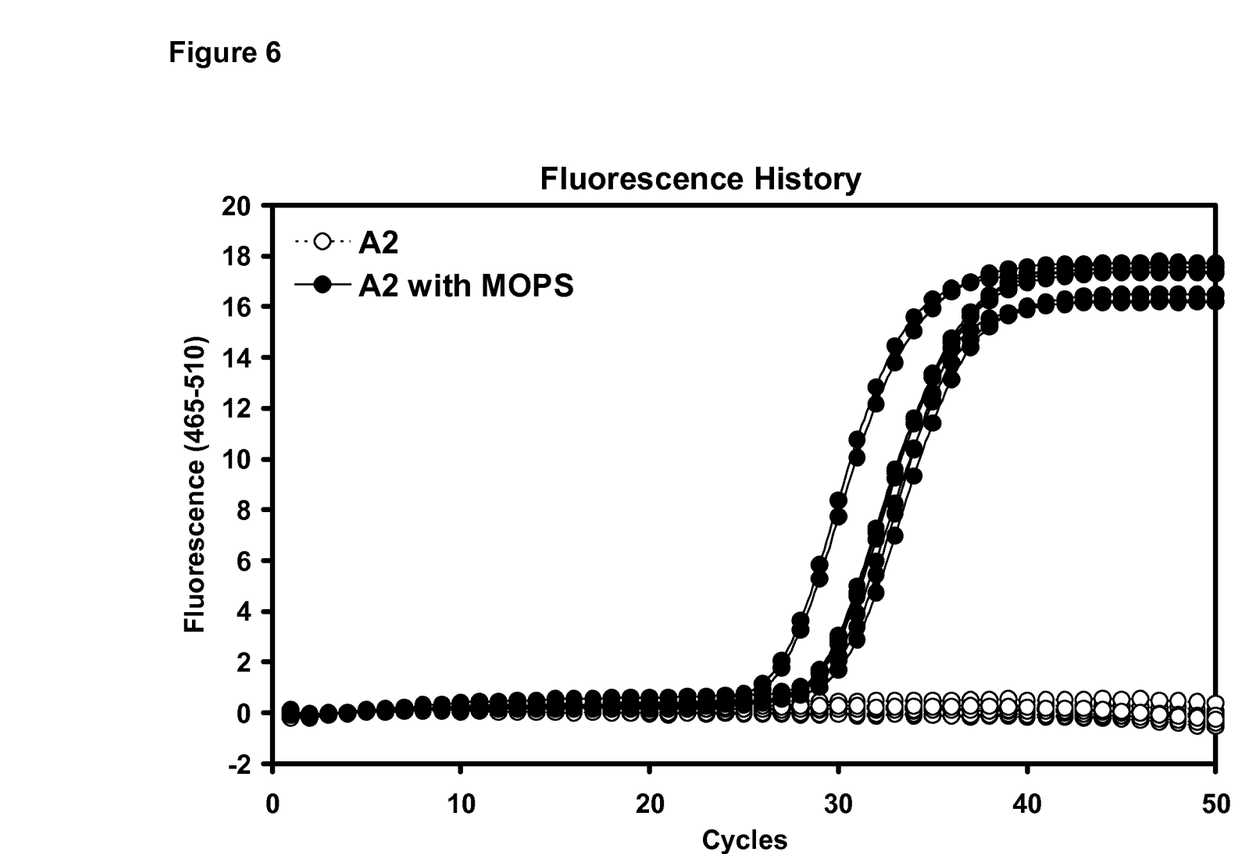
FIG. 6 is a graph illustrating the PCR results of *L. monocytogenes* cultured in Medium A2 or MOPS buffer-added Medium A2 (100 mM MOPS, pH 7.4).

FIG. 6 is a graph illustrating the PCR results of L. monocytogenes cultured in the media A2 or MOPS buffer-added medium A2 (100 mM MOPS, pH 7.4). Referring to FIG. 6, no L. monocytogenes was detected in any of the samples cultured in the Media A2. The initial pH and final pH of the Media A2 were about 6.8 and about 6.5, respectively. Meanwhile, all of the eight samples cultured in the 100 mM MOPS-added Medium A2 (pH 7.4) were detected positive for L. monocytogenes. The average Cp value was about 28.71±1.32. The initial pH and final pH of the MOPS-added Medium A2 were about 7.4. The above results support that the addition of MOPS buffer is advantageous for maintaining the pH of the media and enables detection of L. monocytogenes.

(2) Effect of MOPS Buffer Concentration

First, thirty-two samples, each of 1.5 g ground beef, were inoculated with L. monocytogenes. The samples were cultured at 4° C. overnight. The samples were respectively added into 100 mM, 50 mM, and 25 mM MOPS-added Media A2 (pH 7.4) sterilized by filtration with a 2 μm-membrane filter, or into 100 mM MOPS-added, autoclaved Medium A2 (pH 7.4), and cultured at 30° C. for 24 hours to enrich L. monocytogenes, resulting in eight replicate samples for each medium. The enriched samples were treated with a TZ lysis buffer containing proteinase K to lyse the cells, and cell lysates were analyzed using a forward primer of SEQ NO: 5, a reverse primer of SEQ ID NO: 6, a probe of SEQ ID NO: 7, and an RNase H for L. monocytogenes detection.

As a result, the samples cultured in the 100 mM, 50 mM, and 25 mM MOPS-added, filter-sterilized Media A2 (pH 7.4) had Cp values of about 34.77±2.11, about 34.96±1.89, and about 34.77±2.14, respectively, on average. The samples cultured in the 100 mM MOPS-added, autoclaved Medium A2 (pH 7.4) had a Cp value of about 34.18±1.91 on average. The results show that the concentration of MOPS has almost no effect on the average Cp value. The final pH of the 100 mM and 50 mM MOPS-added, filter-sterilized Medium A2 (pH 7.4) was about 7.4. The final pH of the 25 mM MOPS-added, filter-sterilized Medium A2 (pH 7.4) was about 6.8.

EXAMPLE 5

Effect of Beef Extract on the Growth and Detection of Listeria spp.

Thirty-two samples, each of 1.5 g ground beef, were inoculated with L. monocytogenes. The samples were maintained at 4° C. overnight. The samples were respectively added into the four MOPS-added Medium A2 sterilized by filtration with a 2 μm-membrane filter, three of which respectively further contained 10 g/L of casamino acid, 2.5 g/L TC yeastolate, and 5 g/L of beef extract, and the remaining one contained no additive, and then the mixtures were cultured at 30° C. for 24 hours to enrich L. monocytogenes, resulting in eight replicate samples for each type of medium.

The enriched samples were treated with a TZ lysis buffer containing proteinase K to lyse the cells, and cell lysates were analyzed using a forward and reverse primer of SEQ ID NO: 5, a reverse primer of SEQ ID NO:6, a probe of SEQ ID NO. 7, and an RNase H to detect L. monocytogenes. The PCR conditions were the same as in Example 1, except that FAM was used as donor chromophore.

Figure 7:
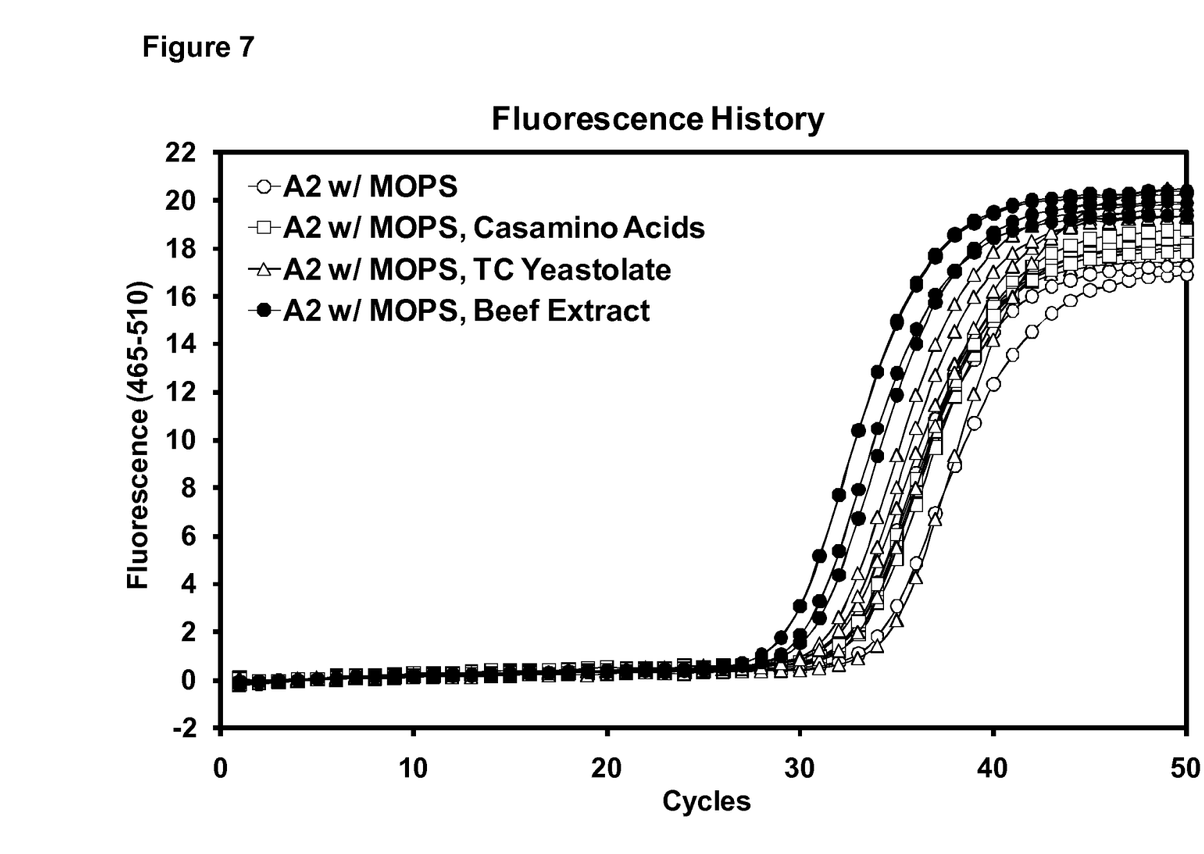
FIG. 7 is a graph illustrating the PCR results of *L. monocytogenes* cultured in Medium A2+MOPS buffer, without beef extract or with beef extract.

As a result, the samples cultured using the MOPS-added Medium A2 respectively further containing no additive, 10 g/L of casamino acid, 2.5 g TC/L yeast isolate, and 5 g/L of beef extract had Cp values of about 31.69±1.21, about 32.16±0.65, about 31.64±1.49, and about 30.94±1.74, respectively, on average. The results, shown in FIG. 7, show that the addition of composite extracts to MOPS-added Medium A2 had almost no effect on the average Cp value, except when the beef extract was added. The addition of the beef extract led to the greatest effect on the average Cp value, reducing the average Cp value by 0.75 cycles. The addition of the beef extract appears to have a slight effect on maximum cell densities, possibly by affecting the recovery of sub-lethally heat-injured Listeria cells by supplying vital growth factors or nutrients.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. An enrichment medium for enhancing growth of *Listeria* a spp., the medium comprising, per 1 L of water, about 10 to about 40 g of tryptic soy broth, about 1 to about 10 g of yeast extract, about 1 to about 10 g of lithium chloride, about 1 to about 5 g of pyruvate or a salt thereof, about 4 g of MOPS free acid, about 7.1 g of sodium MOPS, about 1 to about 10 mg of acriflavine, about 5 to about 15 mg of polymyxin B, about 10 to about 30 mg of ceftazidime, about 0.01 to about 1 g of ferric ammonium citrate, and about 1 to about 10 g of beef extract.

2. The medium of claim 1, wherein the medium does not comprise esculin.

3. The medium of claim 1, comprising, per 1 L of water, about 30 g of tryptic soy broth, about 6 g of yeast extract, about 1 to about 10 g of lithium chloride, about 5 g of beef extract, about 2 g of sodium pyruvate, about 0.2 g of ferric ammonium citrate, about 4 g of MOPS free acid, about 7.1 g of sodium MOPS, about 5 mg of acriflavine, about 10 mg of polymyxin B, and about 20 mg of ceftazidime.

4. A method of enriching *Listeria* spp. in a sample, the method comprising culturing the sample including *Listeria* spp, in a medium comprising, per 1 L of water:

about 10 to about 40 g of tryptic soy broth, about 1 to about 10 g of yeast extract, about 1 to about 10 g of lithium chloride, about 1 to about 5 g of pyruvate or a salt thereof, about 0.01 to about 1 g of ferric ammonium citrate, about 1 to about 10 g of beef extract, about 4 g of MOPS free acid, about 7.1 g of sodium MOPS, about 1 to about 10 mg of acriflavine, about 5 to about 15 mg of polymyxin B, and about 10 to about 30 mg of ceftazidime.

5. The method of claim 4, wherein the medium does not comprise esculin.

6. The medium of claim 4, wherein the medium comprises, per 1 L of water, about 30 g of tryptic soy broth; about 6 g of yeast extract; about 1 to about 10 g of lithium chloride; about 5 g of beef extract; about 2 g of sodium pyruvate; about 0.2 g of ferric ammonium citrate; about 4 g of MOPS free acid; about 7.1 g of sodium MOPS; about 5 mg of acriflavine; about 10 mg of polymyxin B; and about 20 mg of ceftazidime.

7. The medium of claim 1, wherein the medium further comprises a vitamin mix containing about 0.01 to about 0.5 mg of riboflavine, about 0.5 to about 1.5 mg of thiamine, and about 0.01 to about 1.5 mg of biotin.

8. The method of claim 4, wherein the medium further comprises a vitamin mix containing about 0.01 to about 0.5 mg of riboflavine, about 0.5 to about 1.5 mg of thiamine, and about 0.01 to about 1.5 mg of biotin.

* * * * *